(12) United States Patent
Gladden et al.

(10) Patent No.: US 12,142,380 B2
(45) Date of Patent: Nov. 12, 2024

(54) METHOD AND AN APPARATUS FOR BUILDING A LONGEVITY PROFILE

(71) Applicant: Genesis Longevity Bioscience, Rockwall, TX (US)

(72) Inventors: Jeffrey Gladden, Rockwall, TX (US); John Catanzaro, Rockwall, TX (US)

(*) Notice: Subject to any disclaimer, the term of this patent is extended or adjusted under 35 U.S.C. 154(b) by 0 days.

(21) Appl. No.: 18/100,175

(22) Filed: Jan. 23, 2023

(65) Prior Publication Data
US 2024/0249838 A1    Jul. 25, 2024

(51) Int. Cl.
*G16H 50/20* (2018.01)
*G16H 50/30* (2018.01)

(52) U.S. Cl.
CPC ............ *G16H 50/20* (2018.01); *G16H 50/30* (2018.01)

(58) Field of Classification Search
CPC ........ G16H 50/00; G16H 50/20; G16H 50/30; G16H 10/60; G16H 10/40; G16B 20/00; G16B 25/10; G16B 40/00; G16B 50/20; G06N 20/00; G06F 19/12; G06F 19/24
USPC .......................................................... 705/2, 3
See application file for complete search history.

(56) References Cited

U.S. PATENT DOCUMENTS

| | | | | |
|---|---|---|---|---|
| 2008/0220092 A1* | 9/2008 | Dipierro | ................. | A61N 1/30 514/249 |
| 2017/0363618 A1* | 12/2017 | Studer | .................. | A61K 35/30 |
| 2019/0106747 A1* | 4/2019 | Niculescu, III | .... | G01N 33/5085 |
| 2020/0075127 A1* | 3/2020 | Aliper | ................... | G16B 40/20 |
| 2020/0321113 A1* | 10/2020 | Neumann | .............. | G06N 20/00 |
| 2021/0388442 A1* | 12/2021 | Schiederig | ............ | C12Q 1/686 |
| 2022/0005552 A1* | 1/2022 | Galkin | .................. | G16H 50/30 |

FOREIGN PATENT DOCUMENTS

| | | | | |
|---|---|---|---|---|
| WO | WO-2019166859 A1 | * | 9/2019 | |
| WO | WO-2020234729 A1 | * | 11/2020 | ............ A61K 35/28 |
| WO | WO-2021188743 A2 | * | 9/2021 | |

OTHER PUBLICATIONS

López-Otín et al. "The Hallmarks of Aging" https://www.sciencedirect.com/science/article/pii/S0092867413006454 (Year: 2013).*

(Continued)

*Primary Examiner* — Alaaeldin M. Elshaer
(74) *Attorney, Agent, or Firm* — Caldwell Intellectual Property Law

(57) ABSTRACT

An apparatus, and method, for building a longevity profile, the apparatus including at least a processor and a memory communicatively connected to the at least a processor, the memory containing instructions configuring the at least a processor to receive longevity measurement data of a user, where the longevity measurement data includes at least a transcriptomic datum. The processor further configured to determine at least a longevity hallmark as a function of the longevity measurement data and generate a longevity profile of the user of the user as a function of a longevity machine-learning model, wherein the longevity machine-learning model receives the at least a longevity hallmark and the longevity measurement as inputs and outputs the longevity profile, and transmit the longevity profile to an output device.

20 Claims, 10 Drawing Sheets

(56) References Cited

OTHER PUBLICATIONS

Hasin Y, Seldin M, Lusis A. Multi-omics approaches to disease https://www.ncbi.nlm.nih.gov/pmc/articles/PMC5418815/ (Year: 2017).*

Wlaker et al. "Mosaic aging" https://www.researchgate.net/publication/41173470_Mosaic_aging (Year: 2010).*

* cited by examiner

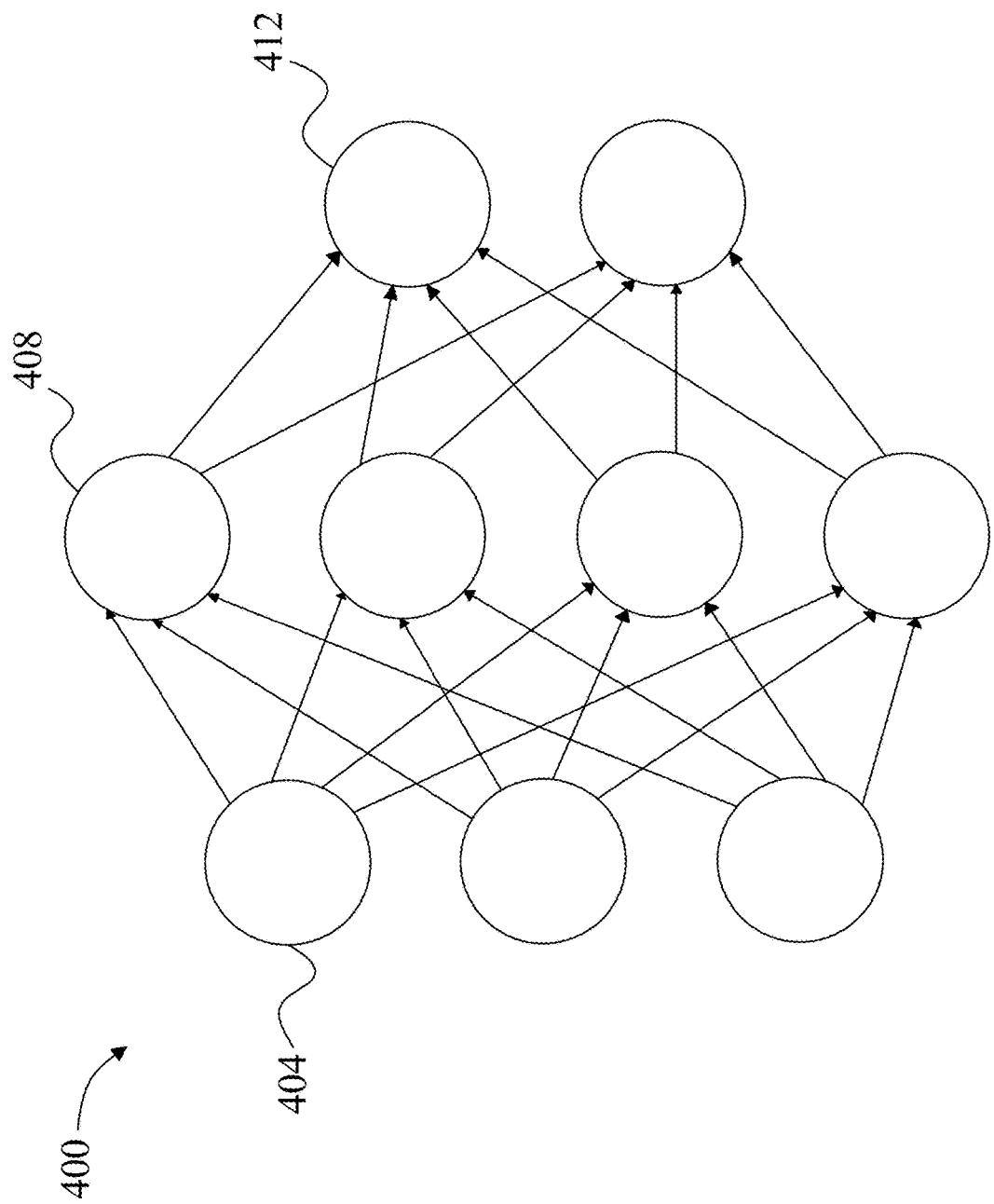

METHOD AND AN APPARATUS FOR BUILDING A LONGEVITY PROFILE

FIELD OF THE INVENTION

The present invention generally relates to the field of personalized healthcare. In particular, the present invention is directed to building a longevity pipeline profile.

BACKGROUND

Detailed reports of a user that identifies specific condition and possible treatments through the use of artificial intelligence is desirable in preventing or assisting in treating a patient in a cost-effective manner.

SUMMARY OF THE DISCLOSURE

In an aspect an apparatus for building a longevity profile, the apparatus including at least a processor and a memory communicatively connected to the at least a processor, the memory containing instructions configuring the at least a processor to receive longevity measurement data of a user, where the longevity measurement data includes at least a transcriptomic datum. The processor further configured to determine at least a longevity hallmark as a function of the longevity measurement data and generate a longevity profile of the user as a function of a longevity machine-learning model, wherein the longevity machine-learning model receives the at least a longevity hallmark and the longevity measurement as inputs and outputs the longevity profile and transmit the longevity profile to an output device.

In another aspect a method for building a longevity profile, the method including receiving longevity measurement data of a user, where the longevity measurement data includes at least a transcriptomic datum and determining at least a longevity hallmark as a function of the longevity measurement datum. The method also including generating a longevity profile of the user as a function of a longevity machine-learning model, wherein the longevity machine-learning model receives the at least a longevity hallmark and the longevity measurement as inputs and outputs the longevity profile, and transmitting the longevity profile to an output device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 4A is an exemplary embodiment of a neural network;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for building a longevity profile for a user. In an embodiment, a method that includes receiving longevity measurement data of a user, where the longevity measurement datum includes at least a transcriptomic datum. The method also includes determining at least a longevity hallmark based on the longevity measurement datum, generating a longevity profile for the user based on the longevity hallmark and the longevity measurement data using a longevity machine learning model and transmitting the longevity profile to an output device.

Aspects of the present disclosure can be used to identify possible conditions of a user. Aspects of the present disclosure can also be used to create treatment plans for a user based on an identified condition. This is so, at least in part, because apparatus and method utilize machine learning models to identify conditions and treatments by using a knowledge dataset.

Aspects of the present disclosure allow for identifying treatment plans that includes a CRISPR gene tool editing. Exemplary embodiments illustrating aspects of the present disclosure are described below in the context of several specific examples.

Figure 1:
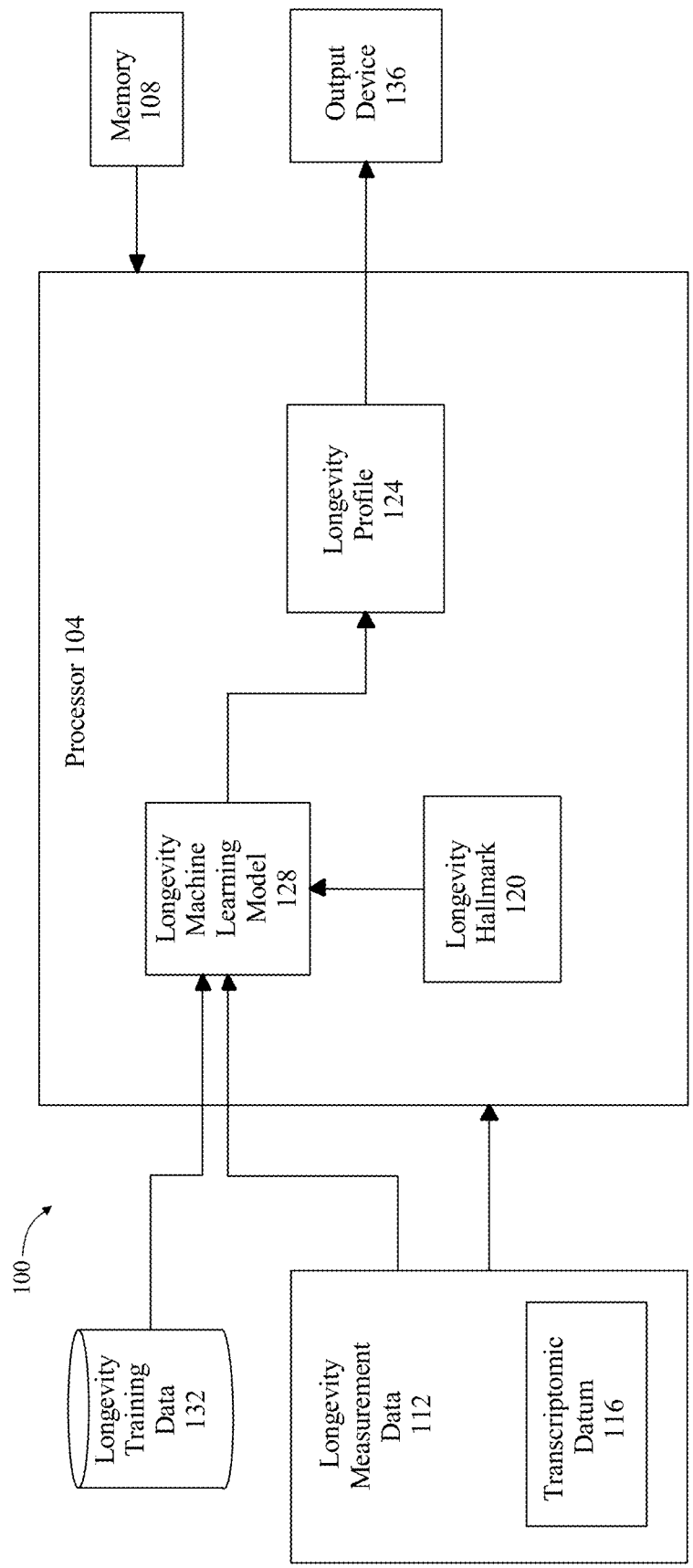
FIG. 1 is an exemplary embodiment illustrating an apparatus for building a longevity profile.

Referring now to FIG. 1, an exemplary embodiment of an apparatus 100 for building a longevity profile is illustrated. Apparatus 100 includes at least a processor 104. Processor 104 may include any computing device as described in this disclosure, including without limitation a microcontroller, microprocessor, digital signal processor (DSP) and/or system on a chip (SoC) as described in this disclosure. Processor 104 may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 1, apparatus 100 includes a memory 108 communicatively connected to the at least a processor 104, wherein the memory 108 contains instructions configuring processor 104 to perform tasks in accordance with this disclosure. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, memory 108 contains instructions configuring processor 104 to receive a longevity measurement data 112 of a user. Processor 104 may receive longevity measurement data 112 from one or more other devices. In an embodiment, processor 104 may perform one or more assessments and/or tests to obtain longevity measurement data 112, and/or one or more portions thereof, on processor 104. For instance, and without limitation, longevity measurement data 112 may include or more entries by a user in a form or similar graphical user interface object, one or more entries may include, without limitation, user responses to questions on a psychological, behavioral, personality, or cognitive tests. In an embodiment, memory 108 may contain instructions configuring processor 104 to present to user a set of assessment questions designed or intended to evaluate a current state of mind of the user, a current psychological state of the user, a personality trait of the user, or the like. In another embodiment, processor 104 may be configured to provide user-entered responses to such questions directly as longevity measurement data 112. In other embodiments, processor 104 may be configured to perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure. In some embodiments, longevity measurement data 112 may include assessment and/or self-assessment data, and/or automated or other assessment results, obtained from a third-party device, where third-party device may include, without limitation, a server or other device (not shown) that performs automated cognitive, psychological, behavioral, personality, or other assessments. Third-party device may include a device operated by an informed advisor. In embodiments, longevity measurement data 112 may include a clinical assessment that includes, without limitation, health screening such as blood pressure, kidney function, electrolyte levels, mental health status, and the like. Clinical assessment may be personalized to the user based on user's overall health status, goals and needs. Clinical assessment may include user's family history, healthcare history, interpersonal relationships, sexual orientation, and the like. Clinical assessment may be extracted from a sample of saliva, urine or the like. Clinical assessment may include exome data, proteomics, biomarkers, hormones, genetic mapping, immune molecular functioning, gene-drug interactions, and the like.

Continuing to refer to FIG. 1, "longevity measurement data," as used in this disclosure, is data containing information related to any biological, chemical, physiological, or other data that is associated with and/or generated by the user, or associated with a non-human biological entity. Longevity measurement data 112 may include a physically extracted sample. A "Physically extracted sample," as used herein, is a sample obtained by removing and analyzing tissue or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example longevity measurement data 112 may include at least a genetic sample. At least a genetic sample may include a complete genome of a person or any portion thereof. At least a genetic sample may include a DNA sample and/or an RNA sample. Longevity measurement data 112 may include an epigenetic sample, a proteomic sample, a tissue sample, a biopsy, and/or any other physically extracted sample. Longevity measurement data 112 may include an endocrinal sample. Longevity measurement data 112 may include medical histories, diseases, surgeries, injuries, symptoms, exercise frequency, sleep patterns, lifestyle habits, and the like, that may be used to inform a user's diet. Longevity measurement data 112 may include dietary information such as nutrition deficiencies, food intolerances, allergies, and the like. Longevity measurement data 112 may include user's lifestyle choices, such as smoker, non-smoker, alcohol levels consumed in a week, workout habits and the like.

Still referring to FIG. 1, longevity measurement data 112 may include a signal from at least a sensor configured to detect physiological data of a user and recording the longevity measurement data 112 as a function of the signal. In an embodiment, at least a sensor may be configured to record longevity measurement data 112 in a knowledge database. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmograph equipment, or the like. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, blood sugar, and/or blood pressure. At least a sensor may be configured to detect internal and/or external biomarkers and/or readings. In a nonlimiting example, longevity measurement data 112 may be detected and recorded through a smartwatch worn by the user. Knowledge database is described in more detail in FIG. 2.

Continuing to refer to FIG. 1, longevity measurement data 112 may include any data suitable for use as physiological state data as described above, including without limitation any result of any medical test, physiological assessment, cognitive assessment, psychological assessment, or the like. Longevity measurement data 112 may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of longevity measurement data 112 consistent with this disclosure.

Still referring to FIG. 1, in embodiments, longevity measurement data 112 may include data, including data as described above, related to a non-human biological entity, such as a domesticated animal. In an embodiment, clinical assessment, as mentioned above, may include an assessment by a veterinary clinic. In a nonlimiting example, longevity measurement data 112 may include a genetic sample of a user's dog.

Continuing to refer to FIG. 1, in embodiments, longevity measurement data 112 may include endogenous metabolism activity that increases stress in the body. Endogenous metabolism activity may include increases and decreases of Amino Acids, fatty acids and other lipids, bile acids, ketone bodies, hormones and other molecules. In some embodiments, longevity measurement data 112 may include exogenous attributes such as stress, levels of radiation, levels of toxins and the like. In some embodiments, longevity measurement data 112 may include correlations between endogenous metabolism activity and exogenous attributes. In a nonlimiting example, longevity measurement data 112 may include high level of exposure to air pollution, such as high concentrations of nitrogen dioxide ($NO_2$), ozone ($O_3$), fine particulate matter <2.5 μm ($PM_{2.5}$), and black carbon (BC) correlated to an abnormal in endogenous metabolism activity, such as decrease production of amino acids associated with downstream effect of increased levels of inflammation.

With continued reference to FIG. 1, longevity measurement data 112 includes at least a transcriptomic datum 116. A "transcriptomic datum," as used in this disclosure, refers to the set of all RNA transcripts, including coding and non-coding, in an individual or a population of cells related to the user. In an embodiment, transcriptomic datum 116 may include RNA transcripts belonging to a non-human species, such as, without limitation, domesticated animals. At least a transcriptomic datum 116 may include transcription and expression levels, functions, locations, trafficking, and degradation of RNA. At least a transcriptomic datum 116 may include the structures of transcripts and their parent genes with regard to start sites, 5' and 3' end sequences, splicing patterns, and posttranscriptional modifications. At least a transcriptomic datum 116 may include all types of transcripts, including messenger RNAs (mRNAs), microRNAs (miRNAs), and different types of long noncoding RNAs (lncRNAs).

Continuing to refer to FIG. 1, in an embodiment, longevity measurement data 112 may include at least a genomic datum. A "genomic datum," as used herein, refers to the complete set of deoxyribonucleic acid (DNA) of an organism, herein referred to as "genome." In some embodiments, an organism's genome may be sequenced. In embodiments, genome sequencing of an organism may include sequencing by synthesis. In embodiments, sequencing by synthesis may include generating a new strand of DNA from a strand of interest by using enzymes in cells that synthesizes DNA (DNA polymerase), where the enzymes are chemically tagged with a fluorescent label. Once chemically tagged, a light source may be used, where the nucleotide is excited by the light source, causing a fluorescent signal to be emitted and detected. In a nonlimiting example, genomic datum included in longevity measurement data 112 may be used to identify genetic variants that are associated with a disease, such as identifying a genetic variant associated with cystic fibrosis.

Still referring to FIG. 1. In some embodiments, longevity measurement data 112 may include at least an epigenomics datum. An "epigenomics datum," as used in this disclosure, refers to a set of chemical modifications to DNA and DNA-associated proteins in a cell, also referred herein as epigenome, which alters gene expression and are heritable through meiosis or mitosis. In a nonlimiting example, changes in the epigenome can switch on or off genes involved in cell growth or the immune response. In this example, epigenomics datum included in longevity measurement data 112 may be used to identify changes in the epigenome that can activate growth-promoting genes in stomach cancer, colon cancer, kidney cancer, and the like.

Continuing to refer to FIG. 1, in an embodiment, longevity measurement data 112 may include an immunophenotyping datum. An "immunophenotyping datum," as used herein, refers to a protein expression used to identify and tag cells, using antibodies, based on the types of antigen or markers on the surface of the cell. In a nonlimiting example, immunophenotyping datum included in longevity measurement data 112 may include a measure of CD4T cell count used to identify immunodeficiency disorders and immune-related diseases. A "CD4T cell," as used herein, is a type of white blood cell.

With continued reference to FIG. 1. In some embodiments, longevity measurement data 112 may include a proteomics datum. A "proteomics datum," as used herein, refers to the protein expressions in a cell, tissue or organism. In a nonlimiting example, proteomics datum included in longevity measurement data 112 may be used to identify protein levels, modification and interactions in a cell, which may be used to assess tumor prognosis, predict tumor classification and to identify potential responders for specific therapies.

Still referring to FIG. 1, in an embodiment, longevity measurement data 112 may include a metabolomics datum. A "metabolomics datum," as used herein, refers to all metabolites present in a cell, tissue, or organism, including small molecules, carbohydrates, peptides, lipids, nucleosides, and catabolic products. A "metabolite," as used herein, is a substance used or made when the body breaks down food, drugs or chemical, and an organism's tissue, such as fat and muscle tissues. In a nonlimiting example, metabolomics datum included in longevity measurement data 112 may be used to identify metabolites associated with external environment and their associations with risks related to a particular disease. In a further nonlimiting example, metabolomics datum may be used to identify a relationship between diet and disease, such as the association between elevated branched amino acids and obesity with an increased resistance to insulin.

Continuing to refer to FIG. 1. In some embodiments, longevity measurement data 112 may include a microbiomics datum. A "microbiomics datum," as used herein, refers to the microbial community (microbiota) composition of a sample such as from human skin, mucosal surfaces and gut. In a nonlimiting example, microbiomics datum included in longevity measurement data 112 may be used to correlate the levels of intestinal microbiota alterations to the onset of metabolic symptoms associated with Type 1 diabetes.

Still referring to FIG. 1, in an embodiment, transcriptomic datum 116 may be obtained by transcribing the DNA of an organism, such as user or a non-human biological entity, by RNA polymerase to create complementary RNA strands, which may then be spliced to remove introns, producing mature transcripts that contain only exons. As used herein, "introns" are non-coding sequences present in the DNA, and "exons" are nucleic acid coding sequences present in mRNA. In a nonlimiting example, transcriptomic datum 116 may be extracted from a user's skin through the use of a dermal biomarker patch (DBP), where the user's sample is extracted and the DNA present in the sample may be transcribed to produce RNA transcripts, as described above.

Continuing to refer to FIG. 1, memory 108 contains instructions further configuring processor 104 to determine at least a longevity hallmark 120 as a function of the longevity measurement data 112. "Longevity hallmark," as used herein, is a biological field that describes the overall health status and longevity of the user. A "biological field," as used herein, is data related to a biological element of an organism, such as user or a non-human biological entity, that can be stored in a dataset. In an embodiment, longevity hallmark may include health status and longevity of a non-human species, such as a domesticated animal. In a nonlimiting example, longevity hallmark 120 may include a user's blood condition such as sickle cell disease. In an embodiment, processor 104 may be configured to determine the at least a longevity hallmark 120 as a function of the at least a transcriptomic datum 116. In some embodiments, the at least a longevity hallmark 120 may be stored in a longevity knowledge database.

With continued reference to FIG. 1, in some embodiments, longevity measurement data 112 may include a combination of transcriptomic datum 116, genomic datum, epigenomics datum, proteomics datum, and/or microbiomics datum, where the combination of two or more are referred herein as "omics." In some embodiments, determining at least a longevity hallmark 120 may include using a multiomics strategy. A "multiomics strategy," as used in this disclosure, is a process that generates a correlation output by analyzing longevity measurement data 112 that includes include a combination of transcriptomic datum 116, genomic datum, epigenomics datum, proteomics datum, and/or microbiomics datum. In a nonlimiting example, multiomics strategy may be used to test correlations between a disease, or factors associated with a disease with longevity measurement data 112, where the different entities of omics data are found to be correlated to specific phenotypes, where the multiomics strategy may provide insight into the role of different factors in disease development. Persons skilled in the art, upon review of this disclosure in its entirety, will be aware of the various ways in which the omics and multiomics strategy may be used to determine at least a longevity hallmark 120.

Still referring to FIG. 1, in an embodiment, longevity hallmark 120 may be determined by using a pathways dataset. In some embodiments, processor 108 may be configured to generate a prediction of overall survival for user. In a further embodiment, longevity profile 124 may be include the prediction of overall survival. "Pathways dataset," as used herein, refers to data of mapped molecular networks of biological systems. Pathways dataset may include the open-source KEGG Pathway Database, developed by Kanehisa Laboratories located in Kyoto, Kyoto Japan. In an embodiment, pathways dataset may be stored in the longevity knowledge database. In an embodiment, processor 108 may be configured to use a single-sample gene enrichment analysis (ssGSEA) to determine the longevity hallmark 120. In some embodiments, processor 108 may be configured to generate longevity hallmark 120 using a pathways dataset and at least a classifier. In some further embodiments, processor 108 may be configured to generate a prediction of overall survival as a function of a machine learning model. A "prediction of overall survival," as used herein, is a predicted chance that the user will survive a diagnosed tumor, described as a percentage. In some embodiments, prediction of overall survival may be described as a range of percentages when multiple machine learning models are used and each of them output varying predicted overall survival for the sample used. Machine-learning models/algorithms are discussed in more detail in FIGS. 3-6.

With continued reference to FIG. 1, pathways dataset may include mapped molecular networks specific to a user. In some embodiments, processor 108 may be configured to generate a prediction of an aging trend as a function of a machine learning model. An "aging trend," as used herein, is a quantitative prediction of the rate of aging of a tested subject. In some embodiments, prediction of aging trend may be described as a range of values when multiple machine learning models are used and each of them output varying predicted aging trends for the sample used. In embodiments, multiomics strategy may be used to identify correlations between a plurality of omics and an aging trend.

Continuing to refer to FIG. 1, in a nonlimiting example, processor 108 may be configured to use a pathways dataset to determine a longevity hallmark 120 that describes a specific type of tumor, where processor 104 may be configured to train and evaluated binary classifiers to predict normal vs tumor sample labels. The binary classifiers may be trained and evaluated using the Cancer Genome Atlas (TCGA) dataset, which includes catalogued molecular and clinical information for normal and tumor samples, and a logistic regression model. Once binary classifier is trained, processor 108 may be configured to train and evaluate multi-label classifiers to predict tumor subtypes using sample-wise pathway activity scores generated by the ssG-SEA, which uses at least a pathways dataset to generate the scores. In this nonlimiting example, processor 108 may determine longevity hallmark 120 as the predicted cancer subtype. Classifiers may be consistent with any classifier described in FIG. 3, and throughout this disclosure.

Still referring to FIG. 1, in an embodiment, processor 108 may be configured to generate a prediction of overall survival as a function of a machine learning model, where the machine learning model takes longevity hallmark 120 as input and outputs the prediction of overall survival. The machine learning model may be trained using training data, where training data correlates predicted cancer subtypes to available treatments. Training data may include TCGA dataset, which includes survival rates for a plurality of tumor subtypes. In a nonlimiting example, processor 104 may determine a grade 2 astrocytoma brain tumor as a longevity hallmark 120, and predict an overall survival rate of 40% based on the correlation of this type of tumor to survival rates for this tumor included in TCGA dataset. Machine learning model may include any machine learning model/algorithm described in FIGS. 3-6 and throughout this disclosure. Persons having ordinary skill in the art, after having reviewed the entirety of this disclosure, will recognize that the uses of pathways datasets described herein are used for illustrative purposes only.

With continued reference to FIG. 1, in an embodiment, determining the at least a longevity hallmark 120 may include using a hallmark machine learning model. Hallmark machine-learning model is configured to receive longevity measurement data 112 as input and outputs at least a longevity hallmark 120. Hallmark machine learning model may include any machine learning model described in this disclosure. In an embodiment, hallmark machine learning model may use a hallmark training dataset. In a nonlimiting example, hallmark training dataset may include longevity measurement data 112 describing hemoglobin compositions in a blood samples correlated to a hemoglobin compositions for sickle cell disease and anemia, where a hallmark machine learning model trained with the hallmark training dataset may determine that user has sickle cell anemia, as longevity hallmark 120. In some embodiments, hallmark training dataset may be stored in a database. In an embodiment, hallmark machine learning model output is stored in a longevity knowledge database. In some embodiments, hallmark training dataset may include past outputs from hallmark machine learning model. In some embodiments, hallmark machine learning model may be configured to utilize a multiomics strategy. In a nonlimiting example, hallmark machine learning model may generate a an aging trend, where hallmark machine learning model receives longevity measurement data 112 that includes a plurality of omics and outputs a longevity hallmark 120 that includes aging trend based on the correlation of omics. In a further nonlimiting example, hallmark machine learning model may be configured to generate alternative aging trends by correlating training data that includes simulated omics with omics included in longevity measurement data 112. Training data and machine learning models/algorithms are described in more detail with respect to FIGS. 3-6.

Still referring to FIG. 1, in some embodiments, hallmark machine learning model may include an in silico model. An "in silico model," as used in this disclosure, is a model that simulate the behavior of cell networks, cancer cells, immunological disease, lung disease, infectious disease, and the like. In an embodiment, in silico model may receive longevity measurement data 112, including at last a transcriptomic datum 116 and at least a proteomics datum, and output longevity hallmark 120, where longevity hallmark 120 includes correlations of transcriptomic datum 116 to proteomics datum. In an embodiment, in silico model may be used to simulate the aging of an organ through correlations of transcriptomic data and proteomics data. In some embodiments, in silico model may be used to simulate an intervention of an aging process through correlations of transcriptomic data and proteomics data. In a nonlimiting example, in silico model may simulate an aging of a cell through correlations transcriptomic data and proteomic data of that cell. In another nonlimiting example, in silico model may predict a decline in physiologic function of an organ due to aging based the composition of transcriptomic data and proteomics data from a sample. In a further nonlimiting example, an aging trend may be predicted by a decrease of a specific mRNA sequence, such as Slc9a3, correlated to the increase of a protein, such as PDZK1. In another further nonlimiting example, an intervention to an aging trend, include in longevity hallmark 120, may be predicted by simulated alteration of levels of mRNA and/or proteins compared to the levels of a predicted aging trend. In an embodiment, processor 104 may be configured to generate an aging trend as a function of longevity measurement data 112, where longevity measurement data 112 includes correlations of endogenous metabolism activity and exogenous attributes. In an embodiment, longevity hallmark may include an aging trend. In a nonlimiting example, processor 104, through hallmark machine learning model, may generate an aging trend above a base level for an individual based on an elevated exposure to a harmful exogenous attribute, such as air pollution, correlated to a reduction in metabolism of glucose and lipids in the body.

Continuing to refer to FIG. 1, in some embodiments, longevity hallmark 120 may be classified using a classifier. In some embodiments, longevity hallmark 120 classified by the classifier may be added to hallmark training dataset. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. The classifier may be configured to output at least a datum that labels or otherwise identifies a set of data that are clustered together, found to be close under a distance metric as described further below, or the like. Processor 104 and/or another device may generate a classifier using a classification algorithm, defined as processes whereby a processor 104 derives a classifier from training data. In some embodiments, the classifier may be trained using classifier training data. Classifier training data may include a plurality of inputs correlated to a plurality of outputs. In some embodiments, classifier training data may include longevity measurement data correlated to longevity hallmarks. In some embodiments, the classifier may be configured to receive a longevity measurement datum as input and classify the longevity measurement datum to a longevity hallmark, wherein the longevity hallmark is output.

Still referring to FIG. 1, processor 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, processor 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 1, in an embodiment, classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. In a nonlimiting example, the classifier may receive sample data for health conditions, such as a diagnosis of a disease, as input and output longevity hallmark 120 associated with the diagnosis of a disease. In another nonlimiting example, the classifier may receive samples of normal and tumor cells as input and output only the tumor cells as longevity hallmark 120. Classifiers are discussed in more detail in FIG. 3, further below.

Still referring to FIG. 1, memory 108 contains instructions further configuring processor 104 to generate a longevity profile 124 of the user as a function of the at least a longevity hallmark 120 and the longevity measurement data 112. A "longevity profile," as used in this disclosure is a detailed analytics report that includes a health status associated with the user. In an embodiment, health status may include the user's immune system health status. In embodiments, health status may include a user's next-generation sequencing (NGS) proteome status. In an embodiment, generating the longevity profile 124 may include using a Precision Based Immuno-Molecular Augmentation (PBIMA) process. "PBIMA," as used herein, refers to an analytical pipeline that uses the results from NGS proteome status, transcriptomic datum 116 and urine proteomics to create specific peptide designs that address identified immune system deficiencies of the patient. In a nonlimiting example, processor 104 may be configured to use the PBIMA analysis pipeline to map and rank potential peptides for effectiveness against a disease indicator determined as a longevity hallmark 120. In some embodiments, processor 104 may be configured to use the PBIMA analysis pipeline to map and rank potential peptides for effectiveness in decelerating an aging trend determined as a longevity hallmark 120. In some embodiments, processor 104 may be configured to use the PBIMA analysis pipeline to map and rank potential peptides for effectiveness in reversing an aging trend determined as a longevity hallmark 120. In an embodiment, generating longevity profile 124 may include using reverse aging, through gene-protein-cell sequence editing, as a function of longevity hallmark machine learning model output. In a further embodiment, longevity profile 124 may include using PBIMA to reverse aging. In a nonlimiting example, processor 104 may be configured to use the PBIMA analysis pipeline to map and rank potential gene sequence editing to reverse aging based on outputs from longevity hallmark machine learning model. In a further nonlimiting example, longevity hallmark machine learning model output may identify accelerated aging process based on a correlation of levels of a certain mRNA sequence to levels of a specific protein, where longevity profile 124 may include instructions to edit the mRNA sequence or modify composition of the specific protein, using PBIMA, as to decelerate the aging process.

With continued reference to FIG. 1, in some embodiments, longevity profile 124 may include a therapy or treatment plan. In further embodiments, therapy plan may include a cell and gene therapy. In embodiments, cell and gene therapy may include a gene editing tool, such as the Clustered Regularly Interspaced Short Palindromic Repeats (CRISPR) gene editing tool. The "CRISPR gene editing tool," as used herein, refers to a component of bacterial immune systems that can cut DNA, which is used as a tool. For example, and without limitations, longevity profile 124 may include a treatment plan for a user that includes treating a sickle cell disease, determined as a longevity hallmark 120, through the use of CRISPR cell editing tool. In an embodiment, longevity profile 124 may include a dietary plan for the user. In some embodiments, treatment plan may include a list of drugs or supplements. In some embodiments, longevity profile 124 may include a lifestyle plan for the user. In an embodiment, longevity profile 124 may include potential diseases the user may have based on the user's health status. In an embodiment, longevity profile 124 may include a PBIMA-PES (Personalized Edited Sequences) report. "PBIMA-PES," as used herein, refers to a custom personalized peptide formulation for the treatment of cancer, neurodegenerative, autoimmune diseases, the like. In an embodiment, longevity profile 124 may include an intervention plan identifying one or more areas for a user to target. In a nonlimiting example, longevity profile 124 may include a PBIMA-PES report recommending a precise set of drugs, natural agents and plant-based medicines for an identified user condition determined as a longevity hallmark 120. In a further example, the identified condition may be aging, where longevity profile 124 may include a PBIMA-PES report recommending a precise set of drugs, natural agents, consumable goods, and plant-based medicines for reversing aging on a user, or target subject. In some embodiments, therapy or treatment plan may be applicable to a non-human species. In a nonlimiting example, treatment plan may include a veterinary procedure for a domesticated animal, such as a cat belonging to a user.

Still referring to FIG. 1, in some embodiments, processor 104 may be configured to compare longevity profile 124 generated to previously generated longevity profile 124. In a nonlimiting example, a newly generated longevity profile 124 may be compared to a prior longevity profile 124 in order to verify that previous treatment plan worked. In a further nonlimiting example, a newly generated longevity profile 124 may be compared to a previous longevity profile 124 that includes an age reversal treatment plan as to verify that target subject's ageing trend has been reversed. In a nonlimiting example, longevity profile 124 may include age reversal for an organ tissue. In another nonlimiting example, longevity profile 124 includes a treatment plan for reversing the age of an entire human subject. In other nonlimiting example, longevity profile 124 includes a treatment plan for reversing the age of a non-human subject, such as a domesticated animal.

Continuing to refer to FIG. 1, generating the longevity profile 124 includes using a longevity machine learning model 128. Longevity machine learning model 128 may include any machine learning model/algorithm described throughout this disclosure and in FIGS. 3-6. Longevity machine learning model 128 receives longevity measurement data 112 and longevity hallmark 120 as inputs, and outputs longevity profile 124. Longevity machine learning model 128 is configured to utilize a longevity training data 132. Longevity training data 132 may include longevity hallmark data and longevity measurement data 112 correlated to associated treatments, such as the therapy or treatment plan discussed above. Longevity training data 132 may include historical data of the user. Longevity training data 132 may include data from open-source datasets. Longevity training data 132 may include clinical assessment data. Longevity training data 132 may include past outputs generated by longevity machine learning model 128. In some embodiments, longevity training data 132 may include data from a longevity knowledge database. In embodiments, longevity training data 132 may include previous outputs of longevity machine learning model 128. In a nonlimiting example, open-source datasets may include the Veradigm Health Insights Ambulatory EHR Database, owned by Allscripts Healthcare LLC, headquartered in Raleigh, NC, USA. Longevity knowledge database is discussed in more detail further below in FIG. 2.

With continued reference to FIG. 1, in some embodiments, longevity machine learning model 128 may be configured to correlate omics included in longevity measurement data 112 and aging trend present in longevity hallmark 120 to training data omics and simulated aging trend. In a further embodiment, processor 104 may be configured to select simulated aging trend with lowest aging trend for the correlation. In another further embodiment, processor 104 may be configured to select simulated aging trend with the highest number for the correlation. In a nonlimiting illustrative example, the correlation may be visualized as two separate puzzle cubes, where a solved cube represents the simulated aging trend and a scrambled cube represents longevity hallmark 120, where there are 20 moves between the scrambled to the solved puzzle cube. In this illustrative example, each move of the scrambled puzzle cube, each move representing a variation of combination of omics, is exponential, where each move is multiplied to the power of 20, which represents each modification of the combination of omics in longevity measurement data 112 multiplied to the power of the total modifications required to achieve the lowest aging trend number, or highest aging trend number.

Still referring to FIG. 1, in some embodiments, longevity profile 124 may include a mosaic aging. A "mosaic aging," as used herein, is an idiosyncratic pattern that reflects the heterogenous effects of aging on molecules, cells, organs, biological systems, and the like. In an embodiment, aging mosaic may include key factors related to aging, such as aging trends based on correlations of endogenous metabolism activity to exogenous attributes, as described above. In some embodiments, mosaic aging may include longevity hallmarks 120 identifying aging of an organ based on correlations of transcriptomic data to proteomics data. In a nonlimiting example, mosaic aging may be used to identify areas in a person's body where aging is progressing faster than other areas. In this example, mosaic aging may identify "weak spots" in a person's body that may be more susceptive to infections, development of cancer and contracting diseases. In a further embodiment, mosaic aging may identify a faster rate of aging in a person's brain cells, which may be used to alert the user of a predisposition for development of dementia. In another nonlimiting example, mosaic aging may be generated for a racehorse, where an identified predisposition to arthritis due to increased aging of the ligaments in the knees may be used by a trained to identify how many more years the horse can race before an injury occurs. Persons skilled in the art, upon review of this disclosure in its entirety, will be aware of the various nonlimiting ways in which mosaic aging may be used to identify aging "weak spots" in the body of a person or non-human organism.

With continued reference to FIG. 1, memory 108 contains instructions configuring processor 104 to transmit the longevity profile 124 to an output device 136. "Output device," as used herein, is a computing device capable of displaying information. In an embodiment, output device 136 may include a plurality of computing devices. Output device 136 may include any computing device included in this disclosure, such as a "smartphone", laptop, tablet, or any other device with capabilities as described herein. In non-limiting exemplary embodiments, output device 136 may display longevity profile 124 via a graphical user interface (GUI). A "graphical user interface," as used in this disclosure, is any form of a user interface that allows a user to interface with an electronic device through graphical icons, audio indicators, text-based interface, typed command labels, text navigation, and the like, wherein the interface is configured to provide information to the user and accept input from the user. Persons skilled in the art, upon review of this disclosure in its entirety, will be aware of the various ways in which an output device 136 may display longevity profile 124 to a user via a graphical user interface, and be aware the various navigation applications that may be used to communicate longevity profile 124.

Continuing to refer to FIG. 1, in an embodiment, longevity profile 124 may be stored in a dataset. In some embodiments, longevity profile 124 may be stored in a longevity knowledge database. In an embodiment, longevity machine learning model 128 may be configured to take a previously generated longevity profile 124 as input in order to generate a new longevity profile. In some embodiments, longevity machine learning model 128 may be trained using longevity training data correlating longevity measurement data and old longevity profiles, to updated longevity profiles. In an embodiment, processor 104 may be configured to compare an existing longevity profile 124 with a newly generated longevity profile 124 and update existing longevity profile 124. In a nonlimiting example, processor 104 may generate a new longevity profile 124, retrieve an existing longevity profile 124 from a database, compare the generated longevity profile 124 to the retrieved longevity profile 124 and update the existing longevity profile 124 based on the comparison, such as updating the longevity profile 124 with the new information included in the newly generated longevity profile 124.

Figure 2:
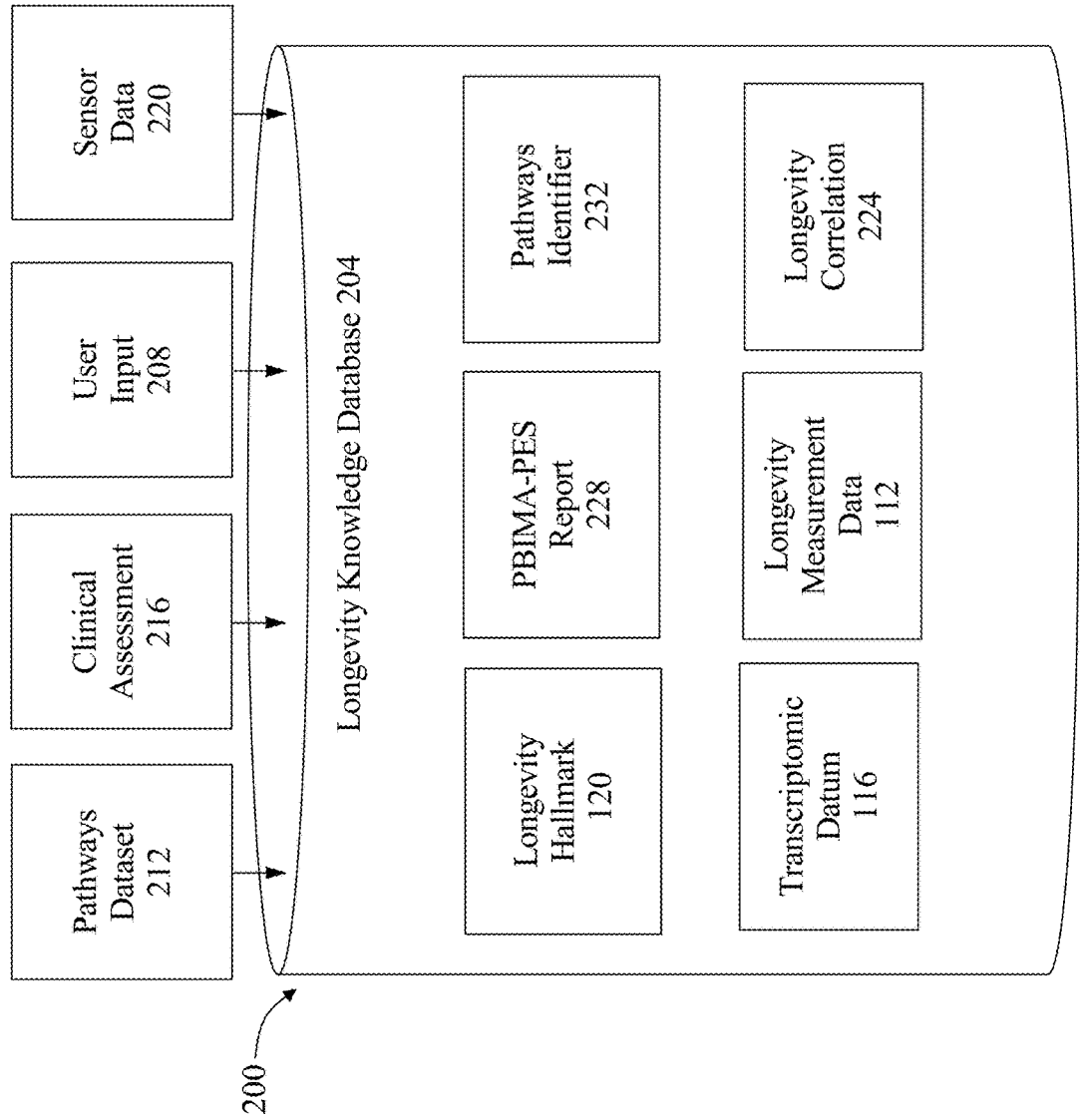
FIG. 2 illustrates an exemplary embodiment of a longevity knowledge database.

Now referring to FIG. 2, a non-limiting exemplary embodiment of a dataset 200 that includes a longevity knowledge database 204 is illustrated. Longevity knowledge database 204 may be implemented, without limitation, as a relational database, a key-value retrieval database such as a NOSQL database, or any other format or structure for use as a database that a person skilled in the art would recognize as suitable upon review of the entirety of this disclosure. Longevity knowledge database 204 may alternatively or additionally be implemented using a distributed data storage protocol and/or data structure, such as a distributed hash table and the like. Longevity knowledge database 204 may include a plurality of data entries and/or records, as described above. Data entries in longevity knowledge database 204 may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Continuing to refer to FIG. 2, longevity knowledge database 204 may receive data from a user input 208. In a nonlimiting example, user input 208 may include information inputted by a user on a form through a GUI in a computing device. In an embodiment, longevity knowledge database 204 may receive data from a pathways dataset 212. In some embodiments, longevity knowledge database 204 may receive data from a plurality of clinical assessments 216. In a nonlimiting example, clinical assessment may include an assessment of a user generated by a healthcare clinic. In embodiments, longevity knowledge database 204 may receive data from at least a sensor 220. In a nonlimiting example, data from at last a sensor 220 may include biometric data gathered by a smartwatch.

Continuing to refer to FIG. 2, one or more data entry cells and/or database tables in longevity knowledge database 204 may include, as nonlimiting example, at least a longevity correlation 224, which may be populated using correlations derived from longevity measurement data 112 as described in further detail above. Longevity correlation 224 may alternatively or additionally be populated in various tables as categorized by themes or other information according to which such correlations may be categorized. In a nonlimiting example, one or more data entry cells and/or database tables in longevity knowledge database 204 may include at least a longevity hallmark 120. In another nonlimiting example, longevity knowledge database 204 may include a PBIMA-PES Report 228. PBIMA-PES report is discussed in more detail in FIG. 1. In nonlimiting examples, longevity knowledge database 204 may include a pathways identifier 232. In a further nonlimiting example, longevity knowledge database 204 may include at least a transcriptomic datum 116. In another nonlimiting example, longevity knowledge database 204 may include longevity measurement datum 112.

Figure 3:
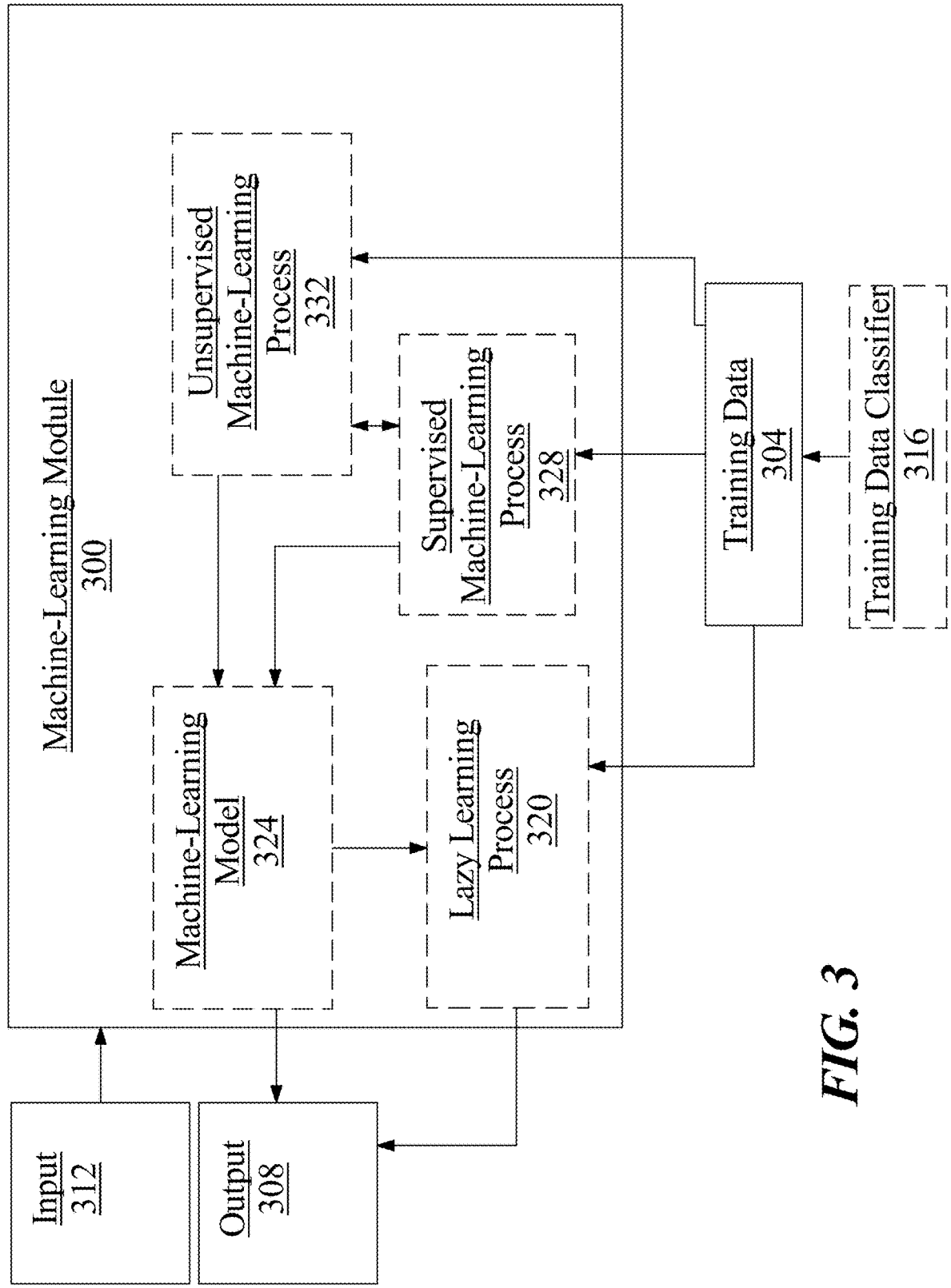
FIG. 3 is an illustrative embodiment of a machine learning model.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example user conditions, such as sickle cell anemia, may be inputs and treatment plans, such as CRISPR gene editing, may be outputs.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to diseases that can be treated through a gene editing tool, such as CRISR.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a blood flow level as described above as inputs, diagnosis of a disease, such as sickle cell condition, as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Referring now to FIG. 4A, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4B:
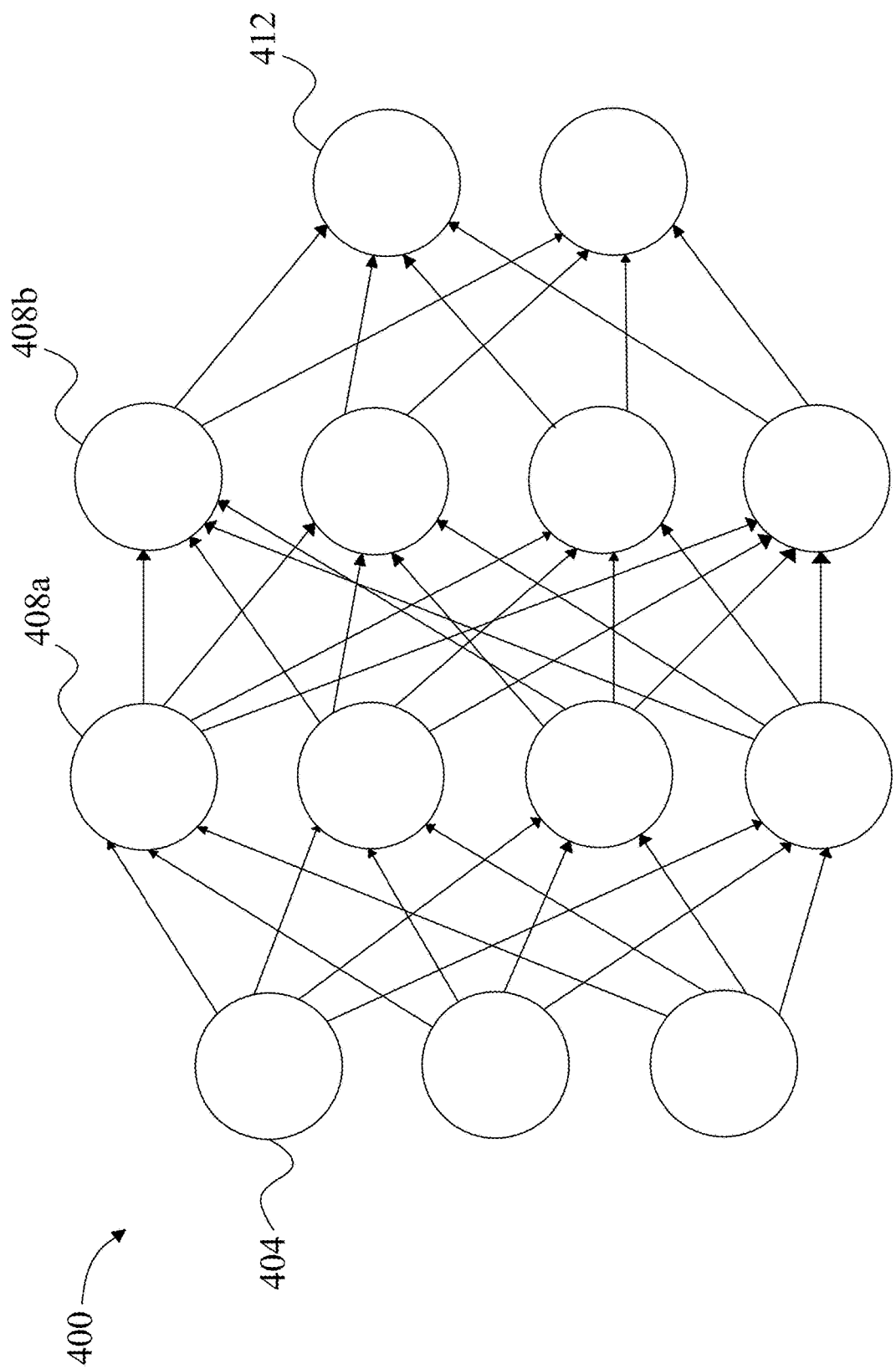
FIG. 4B is an exemplary embodiment of a deep learning neural network.

Referring now to FIG. 4B, an exemplary embodiment of neural network 400 with a plurality of intermediate layers 408, also referred herein as "deep learning", is illustrated. In an embodiment, deep learning neural network 400 may be a feed forward network, wherein the data from input layer of nodes 404 flows to a first layer of intermediate nodes 408a, wherein the output of first intermediate layer 408a flows into a second intermediate layer 408b, wherein the output of second intermediate layer 408b flows into an output layer of nodes 412. In a further nonlimiting example, deep learning neural network 400 may include a backpropagating network where a loss value is calculated by comparing the output of output layer of nodes 412 to an expected output, the loss value then flows back to second layer of intermediate nodes 408b, then to first layer of intermediate nodes 408a. Backpropagation in neural network may be used to adjust weights and bias, described in more detail below. Loss value may be calculated using a loss function, which is described in detail in reference to FIG. 1.

Figure 5:
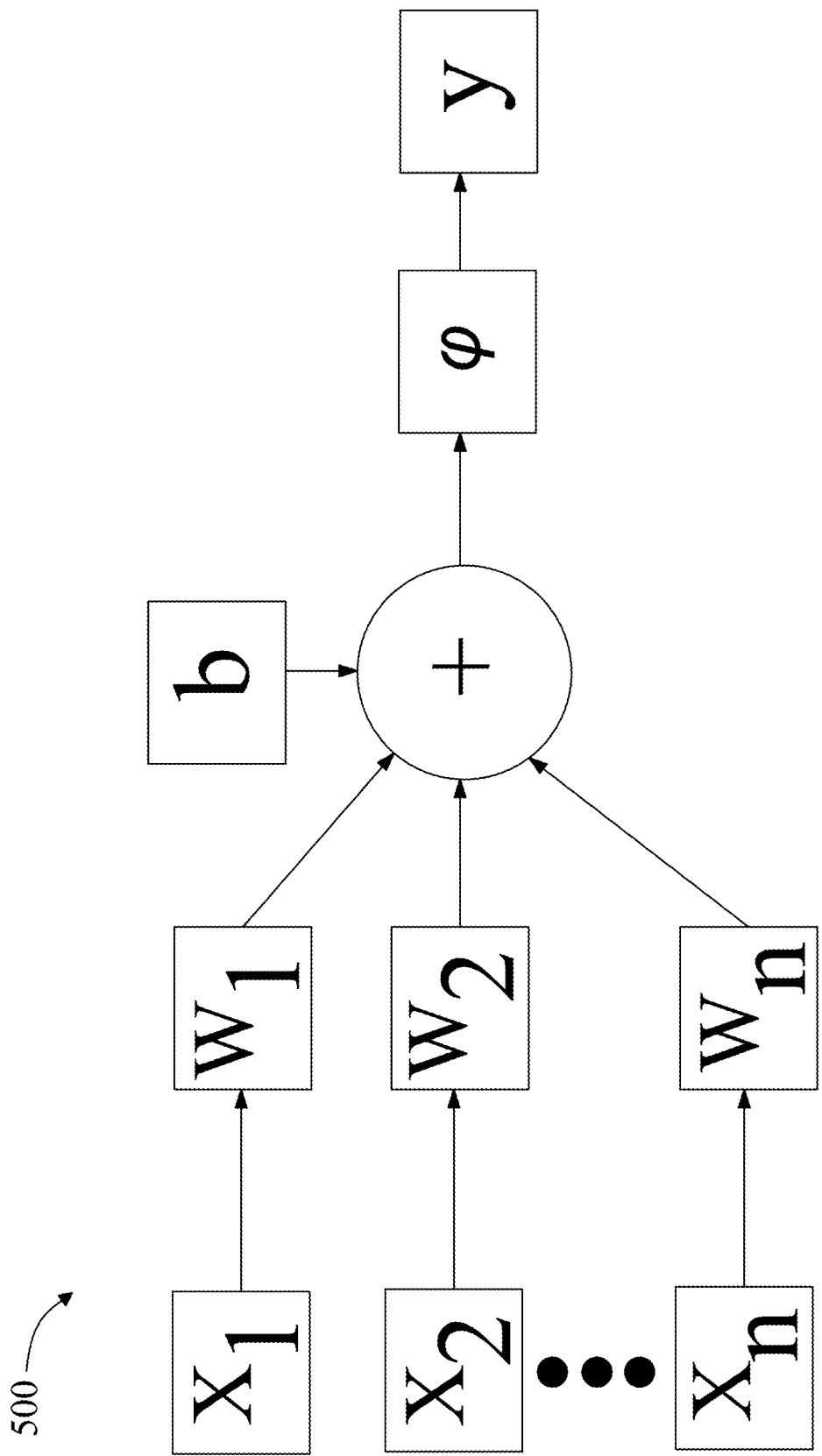
FIG. 5 is an illustrative embodiment of a node of a neural network.

Referring now to FIG. 5, an exemplary embodiment of a node 500 of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$, may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above. In some embodiments Referring to FIG. 6, an exemplary embodiment of fuzzy set comparison 600 is illustrated. A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \leq x < b \\ \frac{c-x}{c-b}, & \text{if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Figure 6:
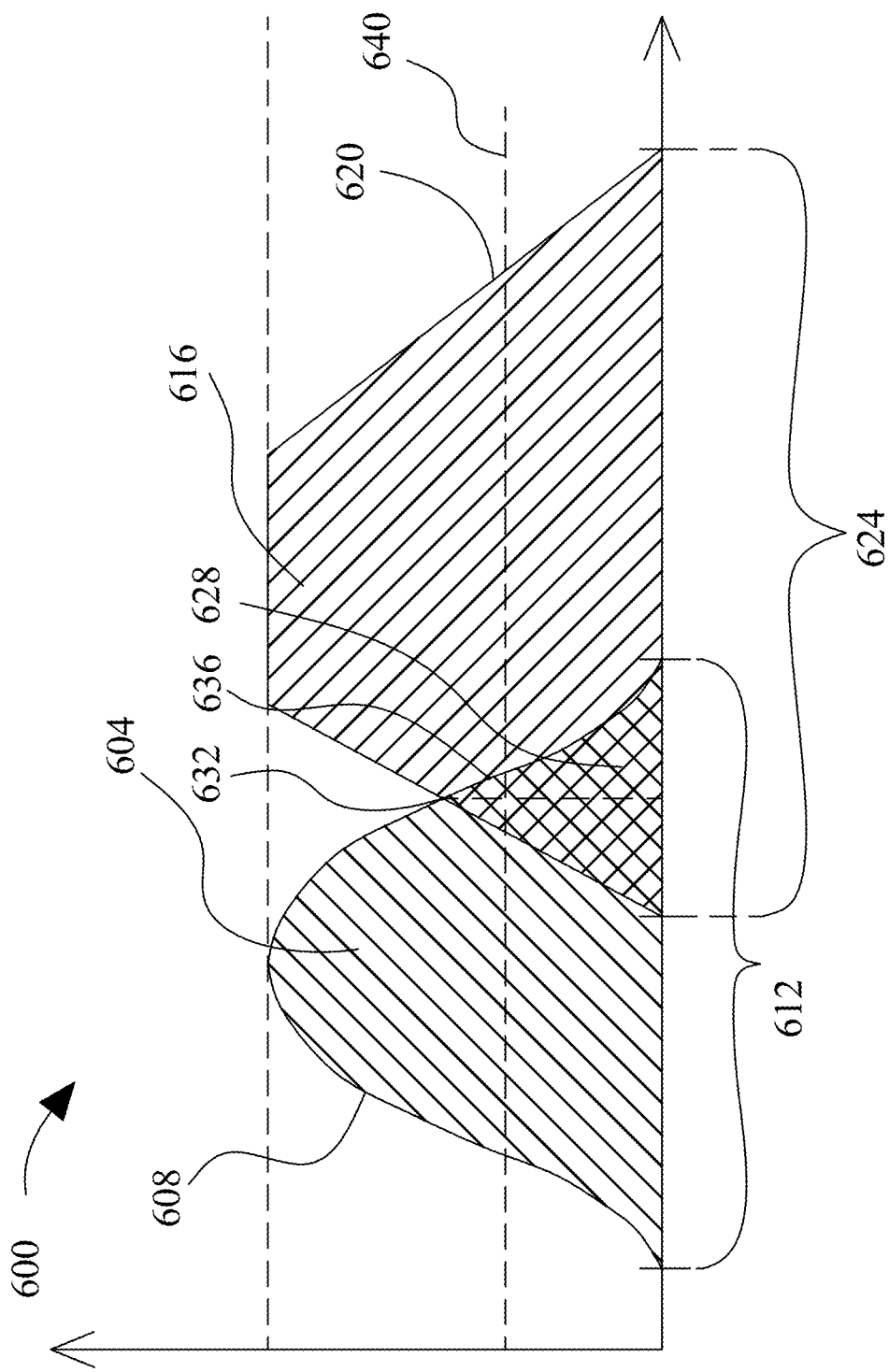
FIG. 6 is a graph illustrating exemplary fuzzy sets.

Still referring to FIG. 6, first fuzzy set 604 may represent any value or combination of values as described above, including output from one or more machine-learning models and longevity measurement data, a predetermined class, such as without limitation a user health state (e.g., healthy, unhealthy, moderate health, poor health and the like). A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 628 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, threshold may indicate a sufficient degree of overlap between an output from one or more machine-learning models and/or a longevity measurement datum and a predetermined class, such as without limitation a user health state, for combination to occur as described above. Alternatively or additionally, each threshold may be tuned by a machine-learning and/or statistical process, for instance and without limitation as described in further detail below.

Further referring to FIG. 6, in an embodiment, a degree of match between fuzzy sets may be used to classify a longevity measurement datum with a user health state. For instance, if a longevity measurement datum has a fuzzy set matching a user health state fuzzy set by having a degree of overlap exceeding a threshold, processor 104 may classify the longevity measurement datum as belonging to the user state. Where multiple fuzzy matches are performed, degrees of match for each respective fuzzy set may be computed and aggregated through, for instance, addition, averaging, or the like, to determine an overall degree of match.

Still referring to FIG. 6, in an embodiment, a longevity measurement datum may be compared to multiple user health state fuzzy sets. For instance, longevity measurement datum may be represented by a fuzzy set that is compared to each of the multiple user health state fuzzy sets; and a degree of overlap exceeding a threshold between the longevity measurement datum fuzzy set and any of the multiple user health state fuzzy sets may cause processor 104 to classify the longevity measurement datum as belonging to a user health state. For instance, in one embodiment there may be two user health state fuzzy sets, representing respectively a healthy state and an unhealthy state. Healthy state may have a healthy state fuzzy set; unhealthy state may have an unhealthy state fuzzy set; and longevity measurement datum may have a longevity measurement datum fuzzy set. Processor 104, for example, may compare a longevity measurement datum fuzzy set with each of healthy state fuzzy set and unhealthy state fuzzy set, as described above, and classify a longevity measurement datum to either, both, or neither of healthy state or unhealthy state. Machine-learning methods as described throughout may, in a non-limiting example, generate coefficients used in fuzzy set equations as described above, such as without limitation x, c, and σ of a Gaussian set as described above, as outputs of machine-learning methods. Likewise, longevity measurement datum may be used indirectly to determine a fuzzy set, as longevity measurement datum fuzzy set may be derived from outputs of one or more machine-learning models that take the longevity measurement datum directly or indirectly as inputs.

Figure 7:
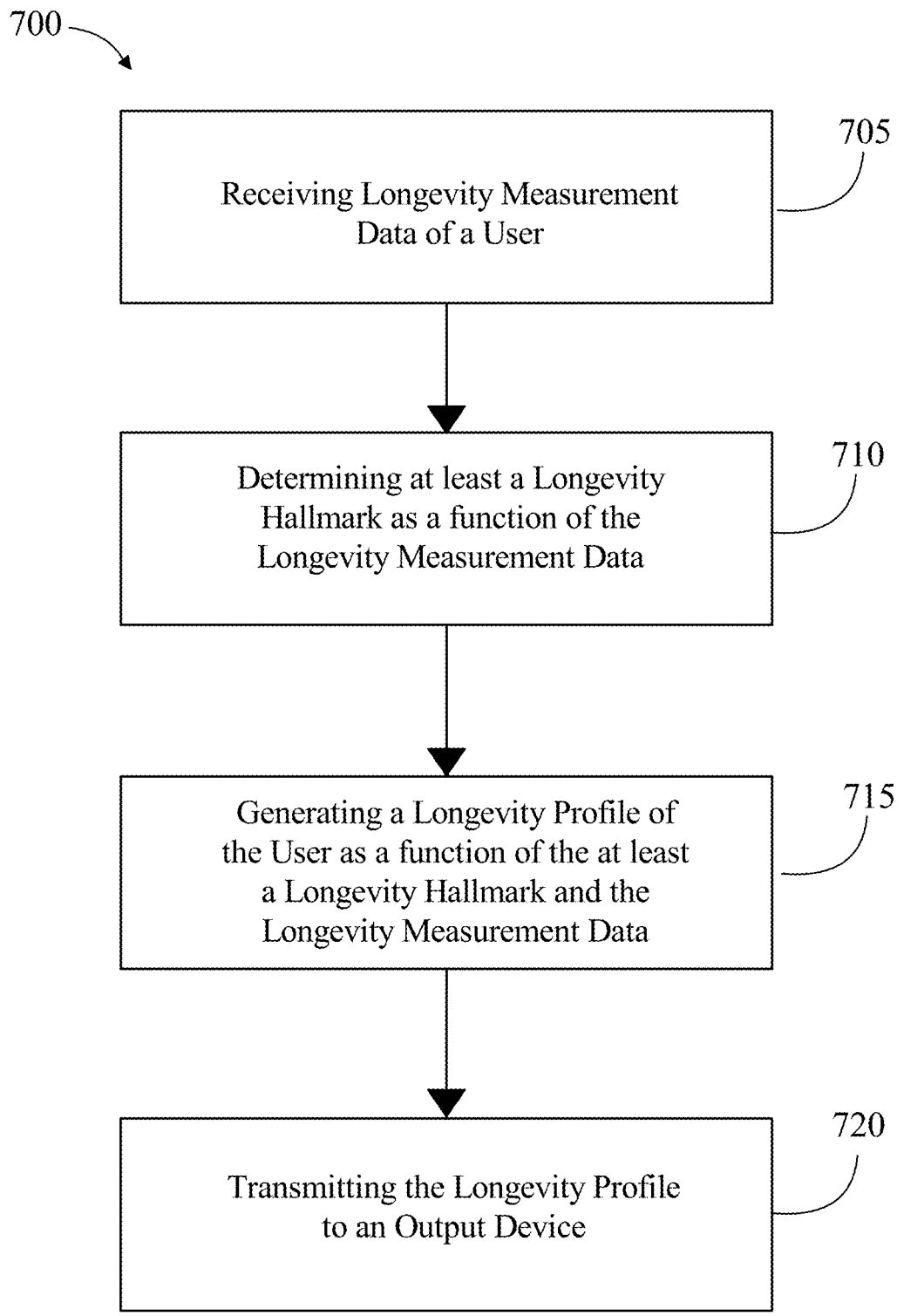
FIG. 7 is an exemplary flowchart of a method for a longevity profile.

Now referring to FIG. 7, a method 700 for building a longevity profile 124 is illustrated. Method 700, at step 705, includes receiving a longevity measurement data 112 of a user, where longevity measurement data 112 includes at least a transcriptomic datum 116. Step 705 may be implemented, without limitation, as described above in reference to FIGS. 1-6.

Continuing to refer to FIG. 7, at step 710, method 700 includes determining at least a longevity hallmark 120 as a function of the longevity measurement data 112. In an embodiment, least a longevity hallmark 120 may be determined as a function of at least a transcriptomic datum 116. In an embodiment, determining the at least a longevity hallmark 120 comprises using a hallmark machine-learning model. In a further nonlimiting embodiment, hallmark machine-learning model may include using a pathways dataset. In an embodiment, determining at least a longevity hallmark 120 may include using the pathways dataset. Pathways dataset is described in more detail in FIGS. 1-2. In a nonlimiting example, method 700 may determine a sickle cell anemia condition for the user, here the longevity hallmark 120, based on a reading of user's blood flow and based on user's RNA sequence that is compared against a pathways dataset. In an embodiment, at least a longevity hallmark 120 may be stored in a longevity knowledge database. In some embodiments, longevity knowledge database may include pathways dataset data. Step 710 may be implemented, without limitation, consistent with references described in FIGS. 1-6.

Still referring to FIG. 7, method 700, at step 715 includes generating a longevity profile 124 of the user as a function of the at least a longevity hallmark 120 and the longevity measurement data 112, where generating the longevity profile 124 includes using a longevity machine-learning model 128. In an embodiment, longevity profile 124 may include a Precision Based Immuno-Molecular Augmentation Personalized Edited Sequences (PBIMA-PES) report. In some embodiments, longevity profile 124 may include a treatment recommendation. In further embodiments, treatment recommendation may include a treatment using Clustered Regularly Interspaced Short Palindrome Repeats (CRISPR) gene editing tool. This step may be implemented as disclosed with reference to FIGS. 1-6.

With continued reference to FIG. 7, at step 720, method 700 includes transmitting the longevity profile 124 to an output device 136. In a nonlimiting example, output device 136 may be a user's smartphone. In another nonlimiting example, output device 136 may be a server, such as a server operated by a healthcare provider. Step 720 may be implemented, without limitation, as described above in reference to FIGS. 1-6.

Figure 8:
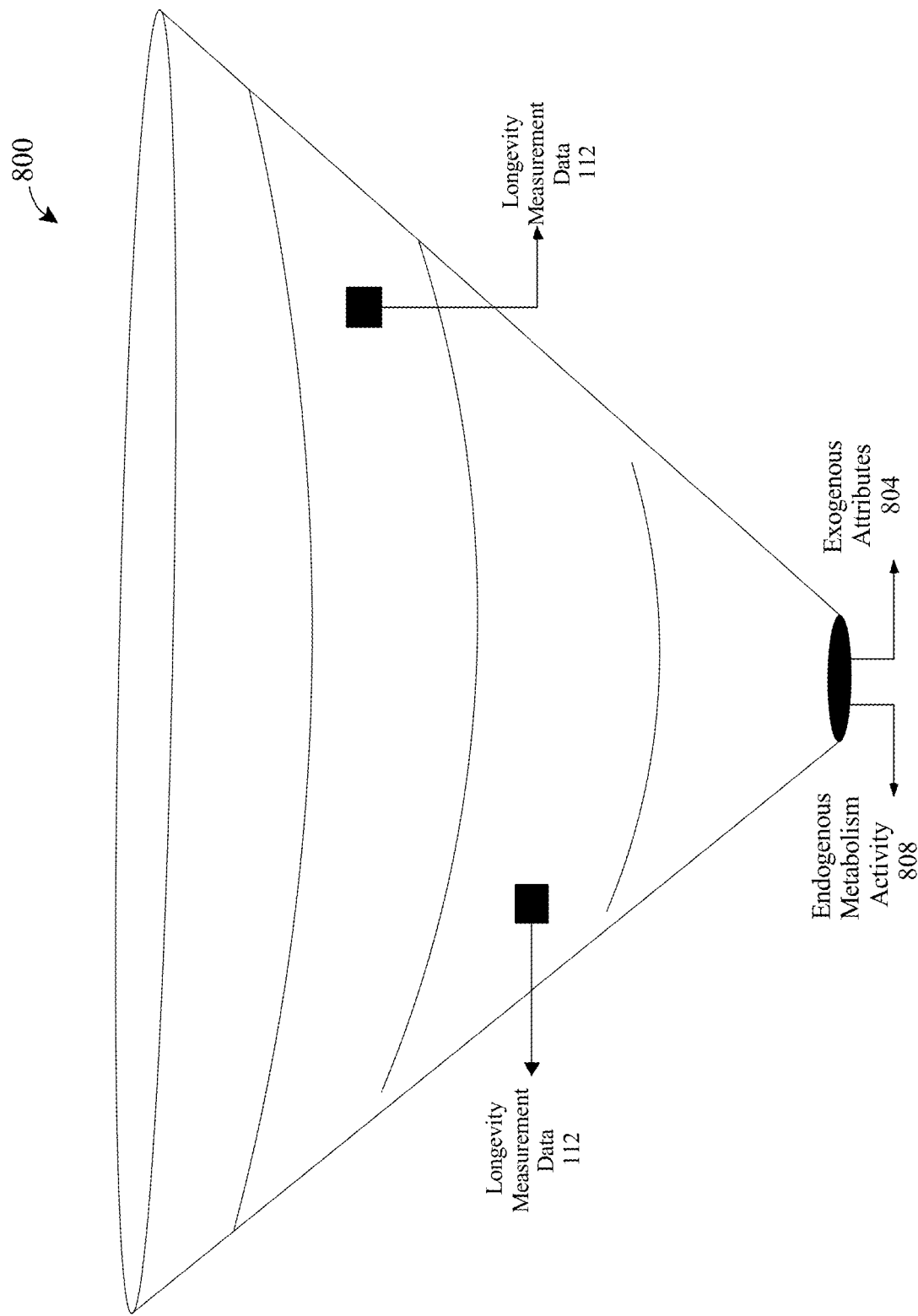
FIG. 8 is an exemplary embodiment illustrating an aging trend.

Now referring to FIG. 8, an exemplary embodiment of an age trend 800 is illustrated as a cloud funnel. In an embodiment, exogenous attributes 804 and endogenous metabolism activity 808 that contribute to an acceleration of the aging trend are represented as the core of a cloud funnel. In this embodiment, longevity measurement data 112 that accelerates the aging trend when combined with exogenous attributes 804 and/or endogenous metabolism activity 808 are represented as the outer edges of the cloud funnel. In this nonlimiting example, as more longevity measurement data 112 that accelerates the aging trend when combined with exogenous attributes 804 and/or endogenous metabolism activity 808 are introduced, the faster the cloud funnel spins, which represents an acceleration of the aging trend.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
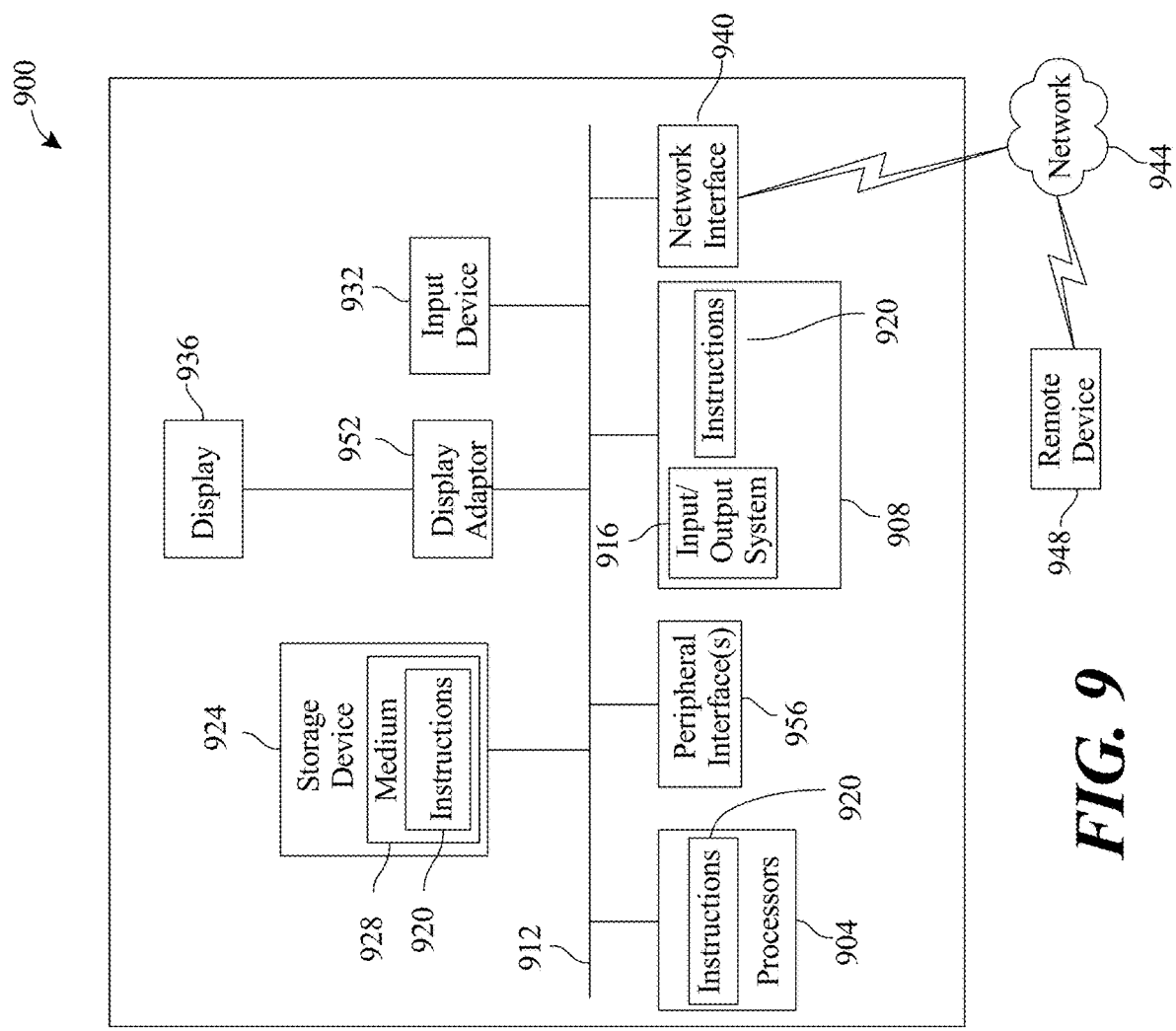
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, apparatus, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for building a longevity profile, the apparatus comprising:
   at least a processor; and
   a memory communicatively connected to the at least a processor, the memory containing instructions configuring the at least a processor to:
   receive longevity measurement data of a user, wherein longevity measurement data comprises at least a transcriptomic datum;
   generate at least a longevity hallmark as a function of the longevity measurement data utilizing a multiomics strategy by:
   training a multi-label classifier to predict tumor subtypes using sample-wise pathway activity scores generated by single-sample gene enrichment analysis (ssGSEA) using a training dataset comprising correlations between tumor subtypes and treatments; and generating the at least a longevity hallmark as a function of the longevity measurement data using the trained multi-label classifier;

wherein the at least a longevity hallmark comprises at least an aging trend, wherein the at least an aging trend comprises a plurality of correlations of endogenous metabolism activity to exogenous attributes;

generate longevity training data as a function of clinical assessment data and a longevity knowledge database, wherein the longevity training data comprises previously generated longevity hallmark data and longevity measurement data correlated to associated treatments, wherein the training data comprises previous outputs of a supervised longevity machine learning model;

train a supervised longevity machine learning model using the longevity training data;

generate a longevity profile of the user as a function of the trained supervised longevity machine learning model, wherein:

the trained supervised longevity machine learning model receives the at least a longevity hallmark and the longevity measurement as input and outputs the longevity profile, wherein the trained supervised longevity machine learning model is configured to correlate the at least a transcriptomic datum and the at least an aging trend to training data omics and simulated aging trends;

the trained supervised longevity machine learning model selects the simulated aging trend with a lowest aging trend for the correlation of the at least a transcriptomic datum and the at least an aging trend to training data omics and simulated aging trends; and the longevity profile comprises a mosaic aging, wherein the mosaic aging comprises an idiosyncratic pattern related to aging that identifies weak spots in a user's body; and transmit the longevity profile to an output device.

2. The apparatus of claim 1, wherein determining the at least a longevity hallmark further comprises using a hallmark machine-learning model, wherein the hallmark machine-learning model receives the longevity measurement data as an input and outputs the at least a longevity hallmark.

3. The apparatus of claim 2, wherein the hallmark machine-learning model is trained using training data comprising a pathways dataset.

4. The apparatus of claim 1, wherein the longevity profile comprises a prediction of overall survival for the user.

5. The apparatus of claim 1, wherein the memory contains instructions further configuring the at least a processor to store the at least a longevity hallmark in the longevity knowledge database.

6. The apparatus of claim 1, wherein determining the at least a longevity hallmark comprises determining the at least a longevity hallmark as a function of the at least a transcriptomic datum.

7. The apparatus of claim 1, wherein the longevity profile comprises a Precision Based Immuno-Molecular Augmentation Personalized Edited Sequences (PBIMA-PES) report.

8. The apparatus of claim 1, wherein the longevity profile comprises a treatment recommendation.

9. The apparatus of claim 8, wherein the treatment recommendation comprises a recommendation regarding using a Clustered Regularly Interspaced Short Palindrome Repeats (CRISPR) gene editing tool.

10. The apparatus of claim 1, wherein the receiving the longevity measurement data of the user comprises receiving the longevity measurement data from at least a sensor.

11. A method of building a longevity profile, the method comprising:

receiving, using at least a processor, a longevity measurement datum of a user, wherein the longevity measurement datum comprises at least a transcriptomic datum;

determining, by the at least a processor, at least a longevity hallmark as a function of the longevity measurement datum utilizing a multiomics strategy by:

training a multi-label classifier to predict tumor subtypes using sample-wise pathway activity scores generated by single-sample gene enrichment analysis (ssGSEA) using a training dataset comprising correlations between tumor subtypes and treatments; and generating the at least a longevity hallmark as a function of the longevity measurement data using the trained multi-label classifier;

wherein the at least a longevity hallmark comprises at least an aging trend wherein the at least an aging trend comprises a plurality of correlations of endogenous metabolism activity to exogenous attributes;

generating, by the at least a processor, longevity training data as a function of clinical assessment data and a longevity knowledge database, wherein the longevity training data comprises previously generated longevity hallmark data and longevity measurement data correlated to associated treatments, wherein the training data comprises previous outputs of a supervised longevity machine learning model;

training, by the at least a processor, the supervised longevity machine learning model using the longevity training data;

generating, by the at least a processor, a longevity profile of the user as a function of the trained supervised longevity machine learning model, wherein:

the trained supervised longevity machine learning model receives the at least a longevity hallmark and the longevity measurement as inputs and outputs the longevity profile, wherein the trained supervised longevity machine learning model is configured to correlate the at least a transcriptomic datum and the at least an aging trend to training data omics and simulated aging trends;

the trained supervised longevity machine learning model selects the simulated aging trend with a lowest aging trend for the correlation of the at least a transcriptomic datum and the at least an aging trend to training data omics and simulated aging trends; and the longevity profile comprises a mosaic aging, wherein the mosaic aging comprises an idiosyncratic pattern related to aging that identifies weak spots in a user's body; and transmitting, by the at least a processor, the longevity profile to an output device.

12. The method of claim 11, further comprising:

generating, by the at least a processor, the at least a longevity hallmark using a hallmark machine-learning model, wherein the hallmark machine-learning model receives the longevity measurement data as an input and outputs the at least a longevity hallmark.

13. The method of claim 12, wherein the hallmark machine-learning model is trained using training data comprising a pathways dataset.

14. The method of claim 11, wherein the longevity profile comprises a prediction of overall survival for the user.

15. The method of claim 11, further comprising:
storing, by the at least a processor, the longevity hallmark in the longevity knowledge database.

16. The method of claim 11, further comprising:
determining, by the at least a processor, the at least a longevity hallmark as a function of the at least a transcriptomic datum.

17. The method of claim 11, wherein the longevity profile comprises a Precision Based Immuno-Molecular Augmentation Personalized Edited Sequences (PBIMA-PES) report.

18. The method of claim 11, wherein the longevity profile comprises a treatment recommendation.

19. The method of claim 18, wherein the treatment recommendation comprises a recommendation regarding using a Clustered Regularly Interspaced Short Palindrome Repeats (CRISPR) gene editing tool.

20. The method of claim 11, further comprising:
receiving, by the at least a processor, the longevity measurement data as a function of at least a sensor.

* * * * *